(12) United States Patent
Hoang et al.

(10) Patent No.: US 12,171,235 B2
(45) Date of Patent: Dec. 24, 2024

(54) ANTIMICROBIAL COMPOSITION AND SYSTEM FOR DELIVERING AN ANTIMICROBIAL COMPOSITION

(71) Applicant: HDR LLC, Park City, UT (US)

(72) Inventors: Minh Hoang, Las Vegas, NV (US); Bryan Garrett Davis, Sandy, UT (US)

(73) Assignee: HDR LLC, Park City, UT (US)

( * ) Notice: Subject to any disclaimer, the term of this patent is extended or adjusted under 35 U.S.C. 154(b) by 69 days.

(21) Appl. No.: 17/712,138

(22) Filed: Apr. 2, 2022

(65) Prior Publication Data

US 2022/0369644 A1 Nov. 24, 2022

Related U.S. Application Data

(60) Provisional application No. 63/184,765, filed on May 5, 2021.

(51) Int. Cl.
| | |
|---|---|
| *A01N 59/12* | (2006.01) |
| *A01N 25/02* | (2006.01) |
| *A01N 59/20* | (2006.01) |
| *A61M 25/00* | (2006.01) |

(52) U.S. Cl.
CPC ............. *A01N 59/12* (2013.01); *A01N 25/02* (2013.01); *A01N 59/20* (2013.01); *A61M 25/00* (2013.01); *A61M 2025/0019* (2013.01)

(58) Field of Classification Search
CPC .............................. A01N 59/12; A01N 25/02; A61M 2025/0019
See application file for complete search history.

(56) References Cited

U.S. PATENT DOCUMENTS

| | | | |
|---|---|---|---|
| 1,719,523 A | 7/1929 | Stephens | |
| 3,542,921 A | 11/1970 | Myatt | |
| 6,482,309 B1* | 11/2002 | Green | C02F 1/46104 204/260 |
| 2003/0194447 A1* | 10/2003 | Scholz | A61K 47/12 424/672 |
| 2005/0262811 A1 | 12/2005 | Mohiuddin | |
| 2005/0271698 A1 | 12/2005 | Bucay-Couto et al. | |
| 2006/0172013 A1* | 8/2006 | Hirai | C23C 26/02 424/630 |
| 2006/0276882 A1* | 12/2006 | Case | A61F 2/07 623/2.18 |
| 2007/0202177 A1 | 8/2007 | Hoang | |
| 2021/0259253 A1 | 8/2021 | Sieracki et al. | |

FOREIGN PATENT DOCUMENTS

WO WO-2021262134 A1 * 12/2021 ........ A61M 25/0026

OTHER PUBLICATIONS

Arendsen et al., The Use of Copper as an Antimicrobial Agent in Health Care, Including Obstetrics and Gynecology, date: Oct. 2019, pp. 1-28, vol. 32, Issue 4, United Kingdom.
Carrillo et al., In Vitro Actinomyces Israelii Biofilm Development, date: Sep. 18, 2009, pp. 261-265, Baja California, Mexico.
Chyderiotis S. et al., New Insights on Antimicrobial Efficacy of Copper Surfaces in the Healthcare Environment- a systematic review, date: 2018. pp. 1130-1138, Nantes, France.
Ghasemian et al., Evaluating the Effect of Copper Nanoparticles in Inhibiting Pseudomonas aeruginosa and Listeria monocytogenes Biofilm Formation, date: May 25, 2014, pp. 5, Isfahan, Iran.
Gomes et al., The Role of Surface Copper Content on Biofilm Formation by Drinking Water Bacteria, date: Oct. 9, 2019, pp. 32184-32196, Braga, Portugal.
Gyawali et al, Antimicrobial Activity of Copper Alone and in Combination with Lactic Acid, date: 2011. pages: 1-10, vol. 2011, Article ID 650968, Greensboro, NC, USA.
Huang et al., In Vitro Efficacy of Copper and Silver Ions in Eradicating Pseudomonas Aeruginosa, Stenotrophomonas Maltophilia and Acinetobacter Baumanni, date: Jul. 3, 2007, pp. 73-80, Kaohsiung, Taiwan.
International Search Report and Written Opinion for PCT/US/2022/27728, dated Aug. 19, 2022, 10 pages.
Pineda, et al., The Role of Copper Surfaces in Reducing the Incidence of Healthcare-Associated Infections- A systematic review and meta-analysis, date: SPRING 2017, pp. 13-24, vol. 3, Issue 1, Santiago, Chile.
Reyes-Jara, Angelica, Antibacterial Effect of Copper on Microorganisms Isolated from Bovine Mastitis, date: Apr. 2016, pp. 10, vol. 7, Madrid, Spain.
Rienzie et al., In Vitro Antimicrobial Properties of Carboxymethyl Cellulose Spray Coated Copper-Montmorillonite Nanocomposites, date: Oct. 2-4, 2017, pp. 1, London, UK.
White et al, Copper Accumulation by Sulfate-Reducing Bacterial Biofilms, date: Dec. 27, 1999, pp. 313/\318, Letters 183, Scotland, UK.

* cited by examiner

*Primary Examiner* — Snigdha Maewall
(74) *Attorney, Agent, or Firm* — James Scott Nolan (57) ABSTRACT

An antimicrobial solution for a medical device having a chamber defined by a wall, the chamber being configured to be includes water, and an amount of iodine in the water sufficient to generate free elemental iodine when introduced into the chamber of the medical device. The free elemental iodine is configured to diffuse through the wall of the chamber and/or be embedded in the wall of the chamber of the medical device to form an antimicrobial polymer on the wall of the chamber.

25 Claims, 6 Drawing Sheets

Figure 1. Schematic diagram of a Foley catheter retained in the bladder by an inflated balloon.

ANTIMICROBIAL COMPOSITION AND SYSTEM FOR DELIVERING AN ANTIMICROBIAL COMPOSITION

CROSS-REFERENCE TO RELATED APPLICATIONS

This application claims the benefit of U.S. Provisional Application No. 63/184,765, filed May 5, 2021. This application is incorporated herein by reference in its entirety.

BACKGROUND

Hospitals, while being a location that renders health care and healing procedures to patients, are also a large source of infections to such patients. Use of medical devices for a medical procedure, or medical procedures themselves, in or on a body of a living being such as a human, can lead to serious nosocomial infections, otherwise known as healthcare- or hospital-associated infections (HAI). HAIs are the direct result of a healthcare-related device or procedure, and are very common, costly, and potentially deadly. HAIs affect 5 to 10 percent, or more, of all hospitalized patients each year in the United States, up to two million patients, and directly account for nearly $50 billion in additional hospital costs, and cause approximately 100,000 or more deaths per year.

Medical devices that are inserted into a living being, such as catheters, must be carefully packaged during manufacturing, and are sterilized to inhibit bacteria or other microbes being present before their use a clinical procedure. Catheters have long been used in hospital settings for infusing fluids such as medicaments, parenteral nutrition and saline solution into a patient. They are also used to withdrawing blood from a patient and monitoring various parameters of the patient's vascular systems. Generally, catheters include a lumen or multiple lumens or reservoirs which contain fluid or medication to be injected or dispensed into the patient's body, and an injection port or device for patient bodily access with a needle.

These lumens and reservoirs can provide large surfaces on which germs, microbes, viruses, and bacteria can colonize and spread. During a medical procedure, as medical devices are inserted into a vein, urethra or other part of a patient, an extraluminal or outer surface of the device can pick up bacteria from the skin and carry the bacteria deep into the insertion site where bacterial colonization may occur.

Catheters come in various forms and types, i.e., central venous catheters (CVCs), intravenous catheters or central venous access devices (CVADs), indwelling catheters, and urinary "Foley" catheters, etc. CVCs and CVADs are often referred to as "central lines" and refer to a broad category of invasive devices used to administer fluids, medications, blood and blood products, and parenteral nutrition. The risks of central line use are significant. Central lines are a major risk factor for bloodstream infection, are associated with a substantial increased risk for infection and mortality, which can drive-up health costs.

Figure 1:
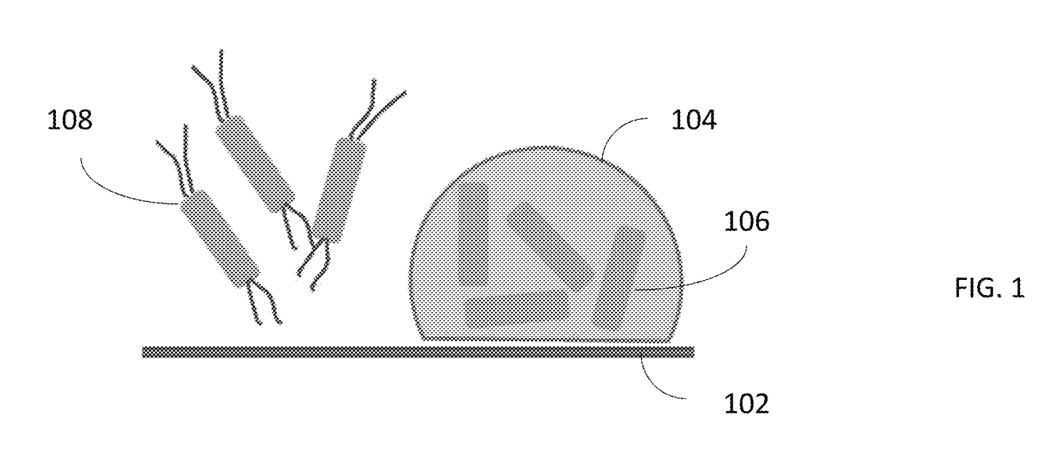
FIG. 1 shows development of a bacterial infection and a biofilm.

The most significant HAIs are those related to invasive procedures and/or medical devices, including, but not limited to: central line-associated bloodstream infections (CLABSI); catheter-associated urinary tract infections (CAUTI); surgical site infections (SSI); and ventilator-associated pneumonia (VAP). As shown in FIG. 1, the smooth, plastic or elastomeric (i.e. balloon) surfaces of a catheter 102, such as a urinary catheter or a central venous catheter, provide an ideal surface for biofilms 104 to attach and grow.

Biofilms are impermeable matrices of low-lying and rapidly reproducing bacteria 106 that are safely encased in their own polymer secretions, and which allow for further reproduction of bacteria and resistance against most antibiotics. These bacteria 106 can grow more rapidly than external bacteria 108 in the environment proximate the catheter surface 102.

In the case of urinary catheters and CVCs, especially those used long term, there is a significant threat of microbial growth along the exterior surface of the catheter. This can lead to CAUTI in the case of long-term urinary catheters (most commonly a Foley catheter) or CLABSI in the cases of CVCs and CVADs. VAP is a lung infection that develops in a person who is on a ventilator. A ventilator is a machine that is used to help a patient breathe by giving oxygen through a tube placed in a patient's mouth or nose, or through a hole in the front of the neck. An infection may occur if germs or other pathogens enter through the tube and into the patient's lungs.

One of the most common healthcare-associated infections is CAUTI, which can occur at any point after urinary catheter placement or removal. Some urinary catheters are known as indwelling catheters that at least partially reside in the bladder, and includes a hollow, flexible tube that collects urine from the bladder and deposits the urine in a drainage bag or other type of basin or container. These catheters are used when a patient cannot empty their bladder, e.g., during surgery or recovery after surgery, and which can be dangerous and lead to permanent kidney damage. Urinary catheters are typically designed for short term use, or can remain "indwelling," i.e. remaining in place for days to weeks. Short term use urinary catheters are known as "intermittent urinary catheters."

A common type of indwelling urinary catheter is known as a "Foley" catheter, which includes an inflatable balloon to secure the catheter tube within the bladder upon insertion. The balloon, after insertion into the bladder, can be inflated with a solution such as sterile water to act as a block against removal of the catheter from the bladder. The smooth, plastic or elastomeric (balloon) surfaces of a Foley catheter provide an ideal nidus for biofilms, as described above and as shown in FIG. 1.

The indwelling urinary catheter is the most commonly deployed prosthetic medical device. It constitutes a convenient way to drain urine from the bladder but unfortunately, also provides a conduit along which bacteria can pass from a heavily contaminated external skin site to infect a vulnerable body cavity. Three primary modes of contamination are extraluminal (during the process of insertion), intraluminal (bacteria growing up the catheter drain lumen), and bacterial seeding of the catheter from bacteria in the urine (can be both intraluminal or extraluminal). The risk of infection is related to the length of time the catheter is in place and for the many catheterized patients, it is inevitable that bacterial communities will establish themselves in the bladder. A variety of organisms commonly colonize the catheterized urinary tract, including *Enterococcus faecalis, Escherichia coli, Providencia stuartii, Pseudomonas aeruginosa, Proteus mirabilis, Morganella morganii* and *Klebsiella pneumoniae*. All urinary catheters have the potential to be colonized, and if the colonization grows to exceed 100,000 colony forming units between days 3 and 16, this highly colonized state is called a Bacteriuria. When a patient has a Bacteriuria with symptoms of infection, this defines a Urinary Tract Infection (UTI).

CAUTI can take the form of bacteriuria (the presence of bacteria in the urine), symptomatic urinary tract infection (SUTI), blood stream infection (BSI), or various combinations thereof. Over 40 million indwelling urinary catheters are inserted in hospitalized patients in the U.S. each year, and in these patients. Colonization of the catheter resulting in asymptomatic bacteriuria occurs in approximately 3-10 percent of patients per day. Once bacteriuria develops, approximately 25 percent of those patients develop symptomatic UTI, and approximately three percent develop bacteremia (the presence of bacteria in the blood) or BSI.

Each case of CAUTI can directly lead to additional hospital costs per patient of between $5,000 to well over $20,000 on average, and typically much more, leading to approximately $4.5 billion in extra costs per year, and over 36 excess deaths for every 1000 in-hospital CAUTI cases. These numbers do not even account for patients for whom a CAUTI is not diagnosed in the hospital, but only later expressed in their home. CLABSI-related additional costs can range from $18,000 to almost $100,000, on average.

Further, since 2008, the Centers for Medicare and Medicaid Services (CMS) no longer reimburses hospitals for the additional costs of caring for patients who develop CAUTI during hospitalization and use of a urinary catheter. Private insurers have also recognized the risks and costs associated with current CAUTI rates, and have exerted significant payment pressures on hospitals when infections occur, as a means to promote infection prevention. Effective infection prevention, however, and especially for CAUTI, remains elusive.

Due to the frequency of catheterization in hospitalized patients, asymptomatic bacteriuria and infection such as CAUTI often precipitate antibiotic therapy, but which in turn may serve as a reservoir for antibiotic-resistant pathogens. The long-term use, and misuse, of antibiotics often results in the rise of antibiotic resistant strains. Hence, in general, systemic antibiotic therapy is ill-advised and ineffective in warding off CAUTI. The secondary side effects of systemic antibiotic treatments can also pose a serious risk to many patients. Microbial biofilms play a significant role in the pathogenesis of infections in all catheters or lumens in direct contact with the body.

As briefly discussed above, after the initial colonization of the abiotic surfaces, pathogens such as bacteria and other uropathogens form hydrated matrices of extracellular polymeric substances known as biofilms. In the case of a CAUTI, these biofilm structures allow for the persistence of bacteria in the urinary tract by facilitating adhesion to the catheter's surface and the patient's epithelium, thus protecting the uropathogens from antibiotics and the host immune system. Bacteria within biofilms can also detach and disseminate from the initial site of colonization to the upper urinary tract, thus being a potential cause of pyelonephritis. Furthermore, uropathogenic bacteria can induce precipitation of calcium and magnesium phosphates, and form urinary stones which may obstruct urine flow through the catheter and lead to serious complications.

While the catheter is in situ, the infections are notoriously difficult to eradicate with antibiotics. It is normal practice to resort to treatment only when there is evidence that the infection has reached the kidneys or the bloodstream. Conceptually, the simplest way to prevent the biofilm formation is to impregnate catheters with a broad-spectrum antimicrobial agent that elutes into the surrounding environment. In this way, illustrated in FIG. 1, planktonic bacteria 108 in the vicinity of the device could be attacked before they colonize the surface and adopt the biofilm-resistant phenotype.

However, difficulties in delivering effective concentrations of antimicrobial agents from catheters for prolonged periods have limited the usefulness of antimicrobial catheters in patients undergoing long-term bladder management, and a common regimen is to change catheters frequently for some that means several days post insertion to periods of up to 10-12 week intervals.

Several attempts have been made to minimize CAUTIs, including the introduction of entirely closed drainage systems and prophylactic treatment with systemic antibiotics. Another approach is to soak the catheter in an antibiotic compound or to cover all of the surfaces with a coating that prevent bacterial adhesion and the production of biofilms. Despite these efforts, CAUTIs are still very common, and the costs for these potentially serious complications are substantial.

Figure 2:
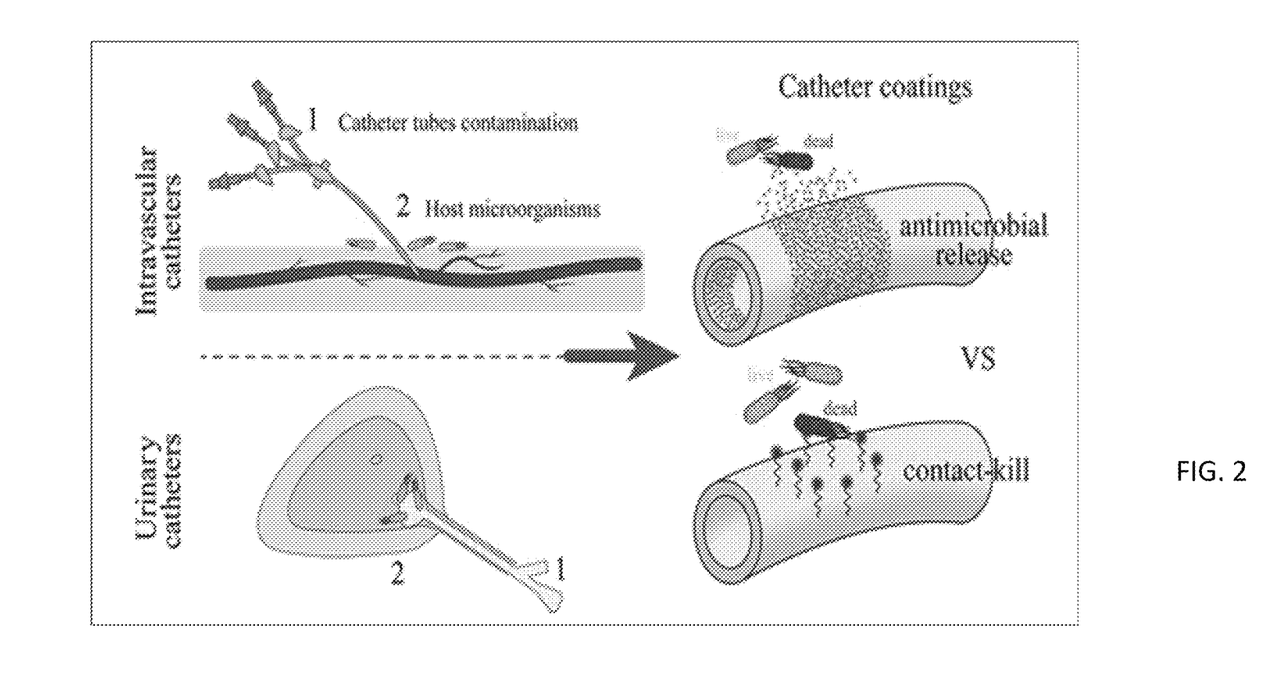
FIG. 2 illustrates antimicrobial agents supplied to catheter material to impregnate the catheter material, such that the catheter material (i.e. tubing) becomes antimicrobial material to prevent the formation of a biofilm or other surface that could host bacterial growth.

Because CAUTIs account for 80% of the total UTIs annually, many infection controls measures have been pursued, such as illustrated in FIG. 2. Though silver hydrogel coatings or impregnation of urinary catheters with antiseptic chemicals such as silver or other antibiotics may reduce the severity of bacteriuria, no methods have yet been developed that effectively prevent biofilm-induced infections associated with the use of Foley catheters. One of the disadvantages of silver-impregnated catheters are that they lose antimicrobial activity over long periods, and therefore are not always suitable for long-term catheterization, and exhibit greater cytotoxicity when compared to antibiotic catheters. However, a major concern regarding the use of antibiotics in urology catheters is the development of resistance of microbes against antibiotics and the cytotoxicity of the antibiotics.

Another proposed solution for preventing infections by the use of tube-containing medical devices, such as urethral catheters, includes the use of a replaceable bioactive luminal structure for insertion into a lumen of the tube-containing medical device. However, this solution requires a metal rod (such as copper) to be contained within the lumen or fluid path, and the question of chemical interactions between infused drugs and the metal rod becomes paramount. Further, this solution requires significant changes to vascular access by necessitating either a massive change to existing access valving or a completely new and additional component.

A key weakness of using such a rod is that it is placed downstream of a potential infection site, and as such, it has to transmit copper ions upstream to affect the pathogenesis of the infection (seeding and growing on the device surfaces in the bladder). The portion of the catheter that ends up on the bladder is the core of the pathogenesis, and the balloon itself represents an overwhelming majority of the surface for the initiation to occur.

Free elemental iodine ($I_2$) is a well-known antimicrobial agent having activity of a broad-spectrum antiseptic with bactericidal, fungicidal, sporicidal and virucidal properties. A few parts per million (ppm) in solution is sufficient to kill bacteria and viruses. Iodine-based products currently in use rely on iodine as the main antimicrobial agent. These products may also be formulated with cationic, anionic or non-ionic or surfactants and skin emollients for skin or topical application purposes. However, because of its high degree of diffusion through water, air and lipids, and its reactivity as an oxidizing agent, elemental iodine is difficult to handle in a clinical setting.

Other problems arise in the use of iodine as an antimicrobial agent. A typical iodine product, whether sterilized or not, continuously loses iodine during its shelf life. Iodophors are generally used in an aqueous base, and, in the presence of water, iodine undergoes a well-known but complex series of reactions leading, among other species, to iodide ions and hydrogen ions. The production of hydrogen ions may reduce the pH of a topical iodine preparation enough to cause skin irritation and discomfort to the user if the iodine was used as surgical scrub or skin prep preparation, but for the antimicrobial filling solution for the balloon catheter, the reduction of pH can support the production of Nitric oxide gas. Loss of iodine titer causes an additional problem of assuring that the iodine content of a composition does not fall below the necessary concentration when this antimicrobial solution is employed, such as being injected into a balloon of a Foley catheter.

Accordingly, a variety of approaches have focused on ways to stabilize the iodine concentration in an iodophor-iodine complex. One approach is directed to a composition that contains an organic material, iodine, iodide ion and iodate ion and is maintained at a pH of from 5 to 7, wherein the iodide and iodate react in the presence of hydrogen ions to replenish iodine lost during storage. Another approach discloses a method to stabilize a preformed iodophor-iodine complex by adding an oxidizing agent, such as iodate ion, and to prepare a complex by reacting an iodophor, such as povidone, with iodate and iodide ions. However, these approaches are not suitable for addressing infections such as CAUTI or other medical device-related infections as they cannot be adequately delivered to a site to prevent the site from becoming a host for the infection.

Copper compounds have been used for their antimicrobial properties since ancient times, and many different microorganisms are rapidly killed by copper ions. Recently, copper alloys have been approved for use by the U.S. Environmental Protection Agency (Reg 82012-1), due to their effective antimicrobial properties, on important bacteria such as methicillin-resistant *S. aureus* (MRSA), *Salmonella enterica*, and *E. coli* 0157, as well as on bacteriophages and Norovirus. Copper is used not only for medical applications but is also used for surfaces, since it can prevent the spread of pathogens more effectively than stainless steel alone or silver. The antimicrobial mechanisms of copper ions include membrane damage, oxidative stress, and protein/DNA denaturation.

The bactericidal activity of copper is mainly attributed to the release of ions, which affect the integrity of the membrane and/or the bacterial wall, generate intracellular oxidative stress and are genotoxic, resulting in the death of microorganisms. Copper is an essential nutrient for humans as well as bacteria, but in high doses, the uncontrolled release of copper ions can cause a series of negative events in bacterial cells, such as disrupting osmotic pressure (osmotic balance), weakening the cell wall and allowing contents to leak out resulting in death of microorganisms. These same toxic effects could happen to human cells if copper is not properly controlled.

Based on the foregoing, there is a critical need for the development of better methods/solution of preventing infections caused with catheter insertions into body cavities, particularly for the development of methods and antimicrobial solution and devices which circumvent the problem of selecting out antibiotic resistant organisms.

SUMMARY

An antimicrobial solution is presented for killing or preventing growth of microbes such as bacteria and viruses, and a delivery system, apparatus and method for the delivery of an antimicrobial solution to prevent biofilm formation in a targeted location within a living being, such as a human. While this document focuses on CAUTIs, it is understood that the present disclosure, and all variations and alternatives described herein, have additional and broad applications in vascular access devices and methods, ventilator tubes, prevention of surgical site infections, general wound or infection care, and the like.

In some aspects, a free iodine-releasing solution is described that can be used to fill a balloon/reservoir with a semiporous membrane, where free iodine is released though the membrane to reduce any microbial attachment to the outer surface of the membrane and/or to reduce bacteria levels that may reside in a fluid surrounding the reservoir.

In other aspects, a free iodine-releasing solution is described that can be used to fill a balloon/reservoir, where the released free iodine attaches to the surfaces of the reservoir and similar or proximate surfaces to form an antimicrobial layer, therefore inhibiting the attachment and growth of bacteria on those surfaces.

In other aspects, an antimicrobial solution includes various compositions of iodine, nitric oxide and copper ion, which can produce free iodine ($I_2$), nitric oxide gas (NO) and copper ion ($Cu^{2+}$) as antimicrobial agents. These compositions can be configured for release into, and eventual withdrawal from, a patient, or a targeted internal area of a patient, by a device that is configured to receive and convey these compositions.

In another aspect, a system and apparatus for delivering an antimicrobial solution into a living being is disclosed. The system and apparatus includes a urinary catheter (e.g., Foley catheter) that prevents encrustation of urine to prevent colonization of bacteria by the catheter. In some implementations, the system and apparatus employ diffusion and/or osmosis of antimicrobial agents of an antimicrobial solution within the retention balloon of the catheter and the communicating lumen.

As discussed above, seeding of bacterial growth needs: 1) bacteria; and 2) area to seed and grow. The present inventions eliminate or stop-quickly-and-reverse the pathogenesis to eliminate the problem of bacteriuria or other bacterial infections. For example, in the case of a Foley catheter, the seeding of interest can be seeding on the portion of a catheter, such as the balloon, that ultimately resides within the bladder. This happens during insertion or shortly after. The present invention quickly attacks these seeds on the indwelling surfaces of the catheter and nearly-within the bladder, to reduce the risk for CAUTI.

In these implementations, a solution or composition provides one or more antimicrobial agents (including but not limited to free iodine, nitric oxide gas, copper ion, or a combination thereof) that are supplied simultaneously, and in various proportions according to application. As applied to a Foley catheter, this can be achieved by a controlled release of the antimicrobial agents from the antimicrobial solution directly into the urine from the catheter balloon and communicating lumen itself, via diffusion and/or osmosis through the wall of the balloon and/or catheter wall. Alternatively, the antimicrobial agents can be impregnated in a material that at least partially forms the catheter, such as the tubing, so the catheter material becomes an antimicrobial material to prevent the formation of a biofilm that could host or colonize bacteria, particularly in a targeted area within the living being.

The details of one or more embodiments are set forth in the accompanying drawings and the description below.

Other features and advantages will be apparent from the description and drawings, and from the claims.

BRIEF DESCRIPTION OF THE DRAWINGS

These and other aspects will now be described in detail with reference to the following drawings.

Like reference symbols in the various drawings indicate like elements.

DETAILED DESCRIPTION

This document describes an antimicrobial composition and delivery system thereof, to kill or stop the growth of microorganisms, such as bacteria and viruses, and to prevent biofilm formation. In some implementations, the delivery system is configured for facilitating a chemical reaction by, or between, one or more chemical components of the composition to produce one or more new antimicrobial components.

In particular implementations, this document describes an antimicrobial solution or substance. In some implementations, the solution or substance can include a single chemical component, such as copper-containing chemical component such as copper sulfate, and/or an iodophor, and/or nitric oxide, or variants thereof.

In some implementations, a solution includes two or more chemical components that produce, via a reduction-oxidation (redox) reaction, one or more new antimicrobial components sufficient for a medical and/or pharmaceutical application. For instance, the one or more new antimicrobial components can include a gas, which is delivered by a delivery system by diffusion and/or osmosis via a surface of the delivery system. In other instances, the one or more new antimicrobial components can include a liquid, cream or gel, for topical application to an infection site, such as mucosal membranes or the like. In still yet other implementations, the one or more new antimicrobial components can be incorporated into a delivery device such as a bandage, applicator, or the like.

In some particular implementations, a free iodine-releasing solution can be used to fill a balloon/reservoir with a semiporous membrane, where the free iodine is released though the membrane to reduce any microbial attachment to the outer surface of the membrane and/or to reduce bacteria levels that may reside in a fluid surrounding the reservoir. In some implementations, the solution can be used to fill a balloon/reservoir, where the released free iodine attaches to the surfaces of the reservoir and similar or proximate surfaces to form an antimicrobial layer, therefore inhibiting the attachment and growth of bacteria on those surfaces.

Accordingly, the present invention includes a medical device fill, lock, flush, irrigation, or topical application solution that includes two or more chemical components that are combined to produce one or more new chemical components via a chemical reaction such as reduction and/or oxidation (redox), and where the one or more new chemical components includes antimicrobial properties.

In some implementations, at least one of the one or more new chemical components is a gas, while in other implementations at least one of the one or more new chemical components is a liquid, and yet in other implementations at least one of the one or more new chemical components is a solid or semi-solid, such as a powder, gel or cream. In some cases, the solution that includes two or more chemical components that are combined to produce one or more new chemical components are contained within the medical device and do not come into contact with a patient's bodily fluids, while in other cases the two or more chemical components are provided in such a way that they directly contact the patient's bodily fluids, such as vascular access or urinary catheter flushing, diffusion and/or osmosis through a selectively permeable membrane, i.e. an inflated catheter balloon, or other deliver mechanism.

Accordingly, while the initial solution may or may not be antimicrobial in its natural state, the chemical reaction is configured to produce one or more antimicrobial agents. Applications can include, without limitation, a cuffed endotracheal tube where a cuff, in the form of a balloon or the like, is filled with an antimicrobial agent such as an antimicrobial gas. Another application can include a rub or ointment. Such an application can be used in a nasal cavity, for example, or other bodily cavity for microbial decolonization. Yet another application can be a rub or ointment for a patient's skin, to inhibit colonization of a biofilm or other infection on the skin. Still yet another application includes applying an implementation of the solution described herein to a bandage or dressing, for such applications as wound care or skin decolonization.

In some implementations, the two or more chemical components and/or the one or more new antimicrobial components can include a copper sulfate fill solution, a PVP-I fill solution, or other inorganic fill solution or fill solution that produces an antimicrobial agent or new component. For instance, in some implementations, an antimicrobial device can include filling a balloon with NO gas, free iodine, or any other antimicrobial gas, or any combination thereof.

Antimicrobial Solution

In some preferred exemplary implementations, an antimicrobial solution for use in a delivery system includes: an iodophor, cupric or copper salt, and sodium nitrite, or various combinations thereof and in various proportions. The iodophor can be PVP-I USP, in powder form, which contains not less than 9% and not more than 12% of available iodine. This iodophor contains some iodide ion, preferably specified at 6.6% or less. The cupric salt can be added to the powder composition. The cupric salt can be any of a number of copper salts such as copper sulfate pentahydrate ($CUSO_4 \cdot 5H_2O$), copper chloride ($CuCl_2$), or any other preferable copper(II) sulfate ($CuSO_4(H_2O)_x$). The sodium nitrite ($NaNO_2$) will oxidize the cupric iodide to release nitric oxide gas (an antimicrobial agent), and the cuprous ion is oxidized back to a cupric ion, and the cupric ion oxidizes the iodide ion to free iodine 12 (another antimicrobial agent).

Iodophor

Iodine is a highly effective topical antimicrobial, with a broad spectrum of antimicrobial activity with efficacy against bacteria, mycobacteria, fungi, protozoa and viruses, but conventionally limited to topical application and treatment of both acute and chronic wounds. In a solution, iodine is generally unstable; at least seven iodine species are present in a complex equilibrium, with molecular iodine ($I_2$) being primarily responsible for antimicrobial efficacy. For instance, or polyvinylpyrrolidone (PVP-I), has broad application for medicine as a surgical scrub, surgical skin preparation, for treatment and prevention of infection in wound, ulcers, cuts and burns. For these applications PVP-I is formulated in an liquid solution, spray, surgical scrub, ointment, and swab dosage form, and is brown in color.

Normal aging converts elemental iodine into iodide ions, thereby causing loss of efficacy. Accordingly, the implementations disclosed herein provide a stability that is adequate for various applications including, but not limited to: 1) antimicrobial balloon filling solutions for a Foley catheter to prevent CAUTI; 2) antimicrobial solutions to irrigate a patient's bladder to prevent CAUTI; and 3) antimicrobial lock solution for CVCs, hemodialysis catheters, and intermittent catheters, etc.

Povidone-iodine is a stable chemical complex of polyvinylpyrrolidone (PVP) and elemental iodine ($I_2$), and acts as a solubilizing agent or carrier called iodophor, which in turn acts as a reservoir of the active "free" iodine. It contains from 9-12% of available iodine. This material contains some iodide ion specified to be 6.6% or less. Combining iodine with polyvinylpyrrolidone (PVP) reduces iodine vapor pressure and increases iodine solubility in water.

In some exemplary implementations, a solution can include copper sulfate and nitric oxide (NO). The color of the composition is initially brown. When all the iodide ion from the PVP-I is oxidized and all the free iodine escapes, the composition will have a blue color from the copper sulfate, since by that time all the sodium nitrite is oxidized, such as by nitric oxide gas (NO), and only copper sulfate is left in the system. The blue color can also act as an indicator that the antimicrobial solution needs to be replaced. At that time, all PVP-I and sodium nitrite have run out of the reaction, and because of this no more free iodine and/or nitric oxide gas is released.

The following is a chemical diagram of an exemplary iodophor in accordance with some implementations described herein:

Nitric Oxide

With a molecular weight of 30, nitric oxide (NO) is one of the smallest biological molecular mediators. In mammalian cells, NO is produced along with 1-citrulline by the enzymatic oxidation of L-arginine. Enzymatically produced NO is important in diverse physiological processes, many of which are relevant to understanding the pathogenesis of infection. NO can contribute to the morbidity of infection by acting as a vasodilator, myocardial depressant, and cytotoxic mediator. On the other hand, microvascular, cytoprotective, immunoregulatory, and antimicrobial properties of NO have a salutary and probably essential role in the infected host.

Normally, NO is produced enzymatically by nitric oxide synthase (NOS) in the presence of oxygen from the amino acid L-arginine. NO is a transitory free radical responsible for the regulation of blood pressure, the control of platelet aggregation, and protection against vascular injury caused by tissue deposition of immune complexes, and is used as a broad spectrum antimicrobial agent by both the innate and cell-mediated immune systems. NO is a free radical that is synthesized in vivo by a family of NOSs that catalyze the oxidation of L-arginine to L-citrulline. There are three nitric oxide synthases produced by eukaryotic cells: (a) endothelial NOS (eNOS), responsible for constitutive NO synthesis in endothelial cells; (b) neuronal NOS (nNOS) responsible for NO synthesis in neural associated cells; and (c) the inducible form, (iNOS), found in epithelial, endothelial, and inflammatory cells, whose expression is upregulated by cytokines, microbes, or bacterial products. NO is synthesized at different levels based on the pathway and the intended function. Much higher levels are required, however, to elicit the bactericidal effects on NO.

NO plays an important role in human-specific and non-specific immunity and that it is a particularly good broad spectrum antimicrobial agent. Evidence for endogenous NO production on skin, within the gut, and by the cellular immune system to protect and fight disease is growing. Furthermore, the importance of systemic nitrate, nitrite, and nitrosylated compounds in blood is becoming better understood and the implications in fighting infectious disease more apparent. Stimulation of endogenous NO or application of exogenous NO to infected human tissue can be an effective method for treating microbial infections; however, considerable hurdles with design of a commercially viable device exist.

One of the largest hurdles in bringing antimicrobial NO-producing products to the clinic is the consistency of gaseous Nitric Oxide (gNO) release at therapeutic levels while maintaining therapeutic antimicrobial levels below what is considered toxic to eukaryotic cells. The majority of adsorption release or chemical release technologies require activation by moisture, heat, light, or other factors that are difficult to control in a clinical setting. These challenges are compounded by the fact that most devices release high levels initially and weaning levels over time making it difficult to ensure bactericidal levels of gNO are sustained for sufficient duration. Consistent delivery of gNO is preferably through direct application of gNO from a tank delivered via tube and/or topical applicator, as disclosed in some implementations described herein.

Unfortunately, this renders patients non-ambulatory and bears significant cost. These hurdles can be overcome with novel gNO activation and delivery systems. In some implementations, controlled release or reaction systems, such as enzymatic systems, provide sustained consistent therapeutic release over time, while utilizing inexpensive mass producible constituents. In addition, these systems and devices are carefully designed with stable and safe components to ensure extended shelf life and stability. Such devices prove commercially viable in treating a wide variety of bacterial, fungal, parasitic, and viral infections, and in healing infected wounds.

Copper

Copper compounds have antimicrobial properties, and many different microorganisms are rapidly killed by copper ions. Recently, copper alloys have been approved for use by the U.S. Environmental Protection Agency (i.e. Reg 82012-1), due to their effective antimicrobial properties, on important bacteria such as methicillin-resistant *S. aureus* (MRSA), *Salmonella enterica*, and *E. coli* 0157, as well as on bacteriophages and Norovirus. Copper is used not only for medical applications, but is also used for surfaces, since it can prevent the spread of pathogens more effectively than stainless steel alone or silver. The antimicrobial mechanisms of copper ions include membrane damage, oxidative stress, and protein/DNA denaturation of bacteria and other microbes.

The bactericidal activity of copper is mainly attributed to the release of copper ions, which affect the integrity of the bacterial wall and/or membrane of bacteria, generate intracellular oxidative stress and are genotoxic, resulting in the death of microorganisms such as bacteria. Copper is an essential nutrient for humans as well as bacteria, but in high doses, copper ions that are released can cause a series of negative events in bacterial cells, including disrupting osmotic pressure (osmotic balance), weakening the cell wall and allowing contents to leak out resulting in death of microorganisms. In the implementations described herein, copper ions are released only in a sufficient amount to act as a bactericide, or to kill or neutralize bacteria or other pathogens or micro-organisms, while being harmless to human cells or cells of other living beings.

Figure 3:
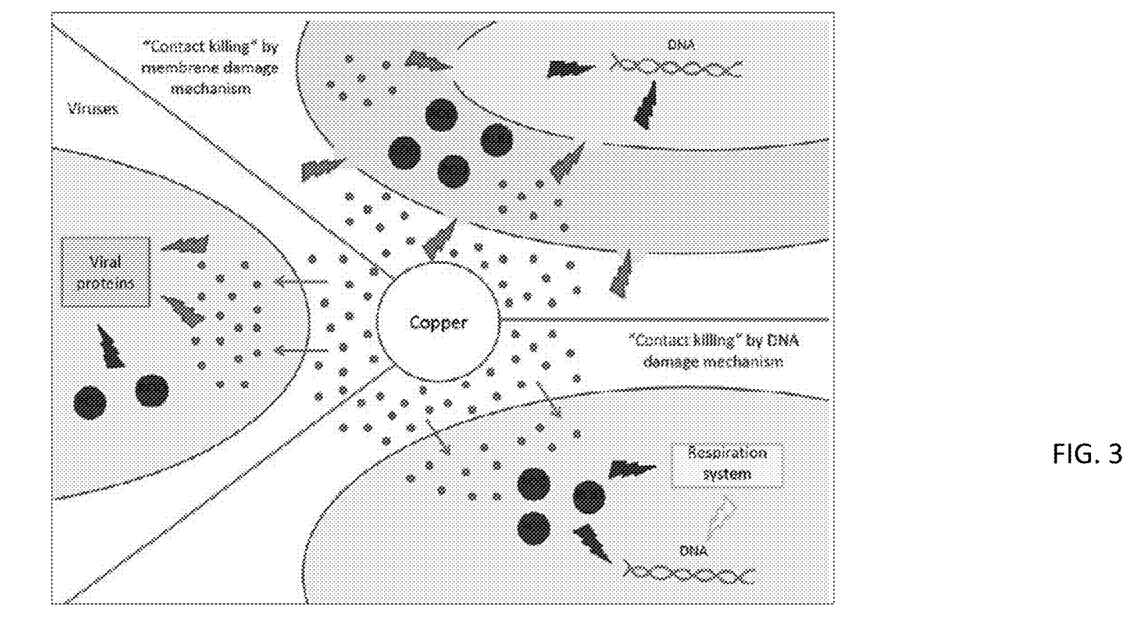
FIG. 3 shows the effects of copper ions released from the solution that inflates the balloon of the urinary catheter, and how copper can kill microbes that might form in the urinary tract of a patient during use of a urinary catheter.

FIG. 3 illustrates the effects of copper ions released from the solution that inflates a balloon of a urinary catheter, and how copper can kill microbes that might form in the urinary tract of a patient during use of a urinary catheter.

The antimicrobials described above are each deliverable in inorganic form, and as such do not require a carrier such as triclosan or other potentially toxic substance.

Organic Antimicrobial Agents

Organic antimicrobial agents that can be used in the presently disclosed implementations include, but not limited to, quaternary ammonium biocides, including pyridinium biocides, benzalkonium chloride, cetrimide, benzethonium chloride, cetylpyridinium chloride, dequalinium acetate, dequalinium chloride. Other organic antimicrobial agents include phenol biocides such as chloroxylenol, parachlorometaxylenol, or 2,4,4'-trichloro-2'-hydroxydiphenol. Antiseptics that can be employed as the biocides used in the present invention include guanidines, such as alexidine, chlorhexidine, chlorhexidine gluconate, chlorhexidine acetate, chlorhexidine hydrochloride, Octenidine dihydrochloride (octenidine) and/or taurolidine.

Solution Example

In preferred exemplary implementations, an iodophor composition produces a stability iodine solution or composition. In some implementations, when the described solution or composition is dissolved in water or an aqueous solution (i.e. urine), or other solvent, other components of the composition, including, but not limited to, PVP-I powder, copper sulfate salt and sodium nitrite salt, completely dissolve. The cupric ion ($Cu^{2+}$) can oxidize the iodide ion ($I^-$) from PVP-I to produce iodine ($I_2$), and this I2 molecule can act as antimicrobial agent to kill any bacteria on contact, as illustrated in Equation (1):

$$2Cu^{2+}+4I^-\rightarrow 2CuI+I_2\nearrow \qquad (1)$$

In some implementations, as shown in Equation (1), the mole ratio is 2 mole of copper sulfate that reacts with 4 mole iodide to produce 2 mole of cuprous iodine (CuI) and 1 mole of free iodine ($I_2$).

This iodide ion ($I^-$) present in the PVP-I solution is converted to iodine ($I_2$) and this free iodine molecule acts as an antimicrobial agent to kill any bacteria it contacts. Further, this iodine molecule will impregnate into any material that it is exposed to or to which it contacts, to make these materials become antimicrobial themselves. Accordingly, these materials will have one or more antimicrobial features, such as killing any bacteria that come into contact with the surface of the material. Additionally, this antimicrobial material will prevent any bacteria from building on the surface, such as or on a biofilm on the surface.

The cuprous iodide (CuI) which is produced in the equation (1) can be oxidized by sodium nitrite in the antimicrobial systems. Nitrite ion $NO^{2-}$ oxidizes cupric iodide (CuI) to produce nitric oxide gas (NO), as according to equation (2):

$$Cu^++NO^{2-}2H^+\rightarrow Cu^{2+}+H_2O+NO\nearrow \text{ gas} \qquad (2)$$

Therefore, 1 mole of cupric iodine can react with 1 mole of sodium nitrite to produce 1 mole of nitric oxide gas. The concentration of the cupric salt is in the range of 0.001% to 0.5% by weight.

The reactions in equations (1) and (2) can occur simultaneously, or sequentially, and the preferred or optimal ratio is formulated to let all the sodium nitrile run out of the system first until no more nitric oxide gas is produced. At that time, only the cupric ion ($Cu^{2+}$) oxidizes the iodide ion (I—) from PVP-I to iodine (I2) until all the PVP-I is run out. The brown color of the iodine solution disappears, and it will be a blue color from the remaining copper sulfate. At this time, the cupric ion ($Cu^{2+}$) will continue to provide the antimicrobial properties. The solution is designed and formulated to change color in a pre-determined number of hours or days after administered, to act as an indicator that it is time to replace the solution and to indicate the working of the antimicrobial effects. Accordingly, the solution can be formulated and configured to change color within 1 to 10 days, or even an hour or more up to and including several weeks.

Consistent with implementations described herein, the iodophor solutions can be prepared by mixing together a source of elemental iodine (such as iodine crystal or PVP-I) with sodium citrate, sodium nitrite, copper sulfate penta hydrate, water and a pH buffer such as sodium citrate or sodium phosphate, or any combination thereof and in any quantity by weight. Finally, the pH of the solution can be adjusted to a desired value ranging from 3 to 6, but preferably a pH of 4-5. Suitable oxidizing agents are iodate, chlorate, nitrite and nitrate, which can be provided in amounts ranging from 0.001% to 0.5% by weight.

In other implementations, an iodophor composition provides a stable iodine solution by adding oxidizing agents such as sodium iodate and/or potassium iodate to the iodine solution, to convert iodide ions into free iodine as elemental iodine. This utilization of iodate can improve the stability of the elemental iodine over period of time. Since iodate contains three oxygen atoms, it is a strong oxidizing agent, generating 3 moles of Iodine per mole of iodate. Iodate react with iodide according to the following reaction in equation (3):

$$IO_3^-+5I^-+6H^+\rightarrow 3I_2+3H_2O \qquad (3)$$

With this iodophor, an aqueous iodophor composition can be prepared such that the amount of elemental iodine ($I_2$) is maintained at a level of between 0.05% to 1.25% by weight and 0.001% to 0.5% by weight of a source of iodate. The source of iodate may be selected from one or more inorganic compounds that include, but not limited to, sodium iodate, potassium iodate, or the like.

In yet another implementation, an iodophor composition can provide a stable iodine solution with added oxidizing agents, such as potassium iodate, to the iodine solution containing copper sulfate, to convert iodide ions into free iodine, or elemental iodine.

$$2CuSO_4 + 4KIO_3 = 2CuI + 2K_2SO_4 + I_2\uparrow \quad (4)$$

In the normal chemical aging process of the iodophor solution, the iodine in the iodophor convert to iodide ions cause the loss of the antimicrobial efficacy of the iodophor solution, by adding the iodate to the iodophor solution which reconvert iodide ions to iodine that make the iodophor regains the antimicrobial efficacy and make the iodophor solution has a longer shelf-life.

Any water-soluble oxidizing agents could be used in the composition in solutions described herein to oxidize iodide ions to elemental Iodine ($I_2$). Suitable oxidizing agents are nitrate, chlorate, peroxide, Iodate, nitrite.

According to some implementations of an iodophor described herein, an aqueous iodophor composition is prepared such that the amount of element iodine ($I_2$) is maintained a level between 0.05% to 1.25% by weight. 0.001% to 0.5% by weight of a source of iodate and the concentration of the cupric salt is in the range of 0.001% to 0.5% by weight. The source of iodate may be select from inorganic compounds that include, but are not limit to sodium iodate and potassium iodate. The iodine solutions in this invention are used on mucous membrane, inside human organs (such as bladder), rinsing open wounds so therefore no surfactants are used. Surfactants and/or other non-essential components may be an irritant, cause an allergic reaction, and/or may be toxic.

Iodophor solution in this invention are preferably prepared by mixing together the source of elemental Iodine (such as iodine crystal or PVP-I), iodate, water and pH buffer such as sodium citrate or sodium phosphate. Finally, the pH of the solution is adjusted to the desired value in the range 3-4. Since normal urine pH is slightly acidic, with usual values of 6.0 to 7.5, but the normal range is 4.5 to 8.0. A urine pH of 8.5 or 9.0 is often indicative of a urea-splitting organism, such as *Proteus, Klebsiella*, or Urea plasma *urealyticum*. An alkaline urine pH can signify struvite kidney stones, which are also known as "infection stones." Urinary tract infections (UTIs) are one of the most common indications for antibiotics in both the inpatient and outpatient setting. A recent review article stated imaging should be considered for patients with a urinary pH of 7 or higher. Alkaline urine was defined as a urinary pH greater than or equal to 7, while acidic urine was defined as a urinary pH less than 7. Patients with alkaline urine are more likely to have recurrence of UTI.

The iodine solution preferably has a pH in the range of 3-6, such that the iodophor will have strong antimicrobial efficacy when it is used as a bladder irrigation to kill all the bacteria in an infected bladder, or used for filling the balloon of a Foley catheter to prevent catheter colonization and prevent the biofilm formation on the catheter tip.

Controlling the pH of the iodophor solution prolongs the shelf-life of the iodophor solution and also achieves other antimicrobial efficacy benefits for medical applications. Control of the pH may be augmented by adding a buffer to maintain the pH of the solution in the range of 3-6 and preferably a pH of 4-5. Suitable buffers include, without limitation, sodium acetate, ammonium acetate, sodium citrate, sodium phosphate dibasic heptahydrate, citric acid (such as sodium citrate buffer and citric acid), and sodium phosphate dibasic.

A portion or all of the above-described solutions or compositions can be provided as a solid, such as a powder, or as a semi-solid such as a gel or cream, or as a liquid. Each of these states can be used, inter alia, as a topical rub or application, or as a fill solution for a medical device, i.e. for filling a balloon of a Foley catheter, for example.

The table below illustrate exemplary implementations of a solution and formulation thereof, for a medical device fill, lock, flush or topical solution to provide antimicrobial properties and effects via components of the solution.

TABLE 1

| Ingredients | Formula Zero Control PVP-I | Formula 1 | Formula 2 | Formula 3 | Formula 4 | Formula 5 | Formula 6 | Formula 7 |
|---|---|---|---|---|---|---|---|---|
| PVP-I | 2.00 | 5.00 | 5.00 | 5.00 | 5.00 | 2.00 | 2.00 | 2.00 |
| Sodium Citrate | 0.00 | 1.00 | 1.00 | 1.00 | 0.50 | 1.30 | 1.09 | 0.62 |
| Copper Sulfate penta hydrate | 0.00 | 0.50 | 1.68 | 0.50 | 1.00 | 1.50 | 1.52 | 1.00 |
| Sodium Nitrite | 0.00 | 1.25 | 3.00 | 0.66 | 1.00 | 1.00 | 1.00 | 1.00 |
| Potassium Iodate | | | | | | | | |
| Potassium Iodide (KI) | | | | | | | | |
| Water | 98.00 | 92.20 | 89.30 | 92.80 | 92.50 | 94.20 | 94.40 | 95.40 |
| HCl | q.s. | q.s. | q.s. | q.s. | q.s. | q.s. | q.s. | q.s. |
| Total | 100.0 | 100.0 | 100.0 | 100.0 | 100.0 | 100.0 | 100.0 | 100.0 |

| Ingredients | Formula 8 | Formula 9 | Formula 10 | Formula 11 | Formula 12 | Formula 13 | Formula 14 | Formula 15 |
|---|---|---|---|---|---|---|---|---|
| PVP-I | 2.00 | 1.00 | 1.00 | 1.00 | 1.00 | 3.1 | 3.0 | 2.00 |
| Sodium Citrate | 0.50 | 1.00 | 1.04 | 0.55 | 0.56 | 0.5 | 1.0 | 1.00 |

TABLE 1-continued

| Ingredients | | | | | | | | |
|---|---|---|---|---|---|---|---|---|
| Copper Sulfate penta hydrate | 1.00 | 1.55 | 1.00 | 1.00 | 0.63 | 0.2 | 1.0 | 0.05 |
| Sodium Nitrite | 1.16 | 1.13 | 1.00 | 1.00 | 0.59 | 1.0 | 1.5 | |
| Potassium Iodate | | | | | | | | 0.10 |
| Potassium Iodide (KI) | | | | | | | | |
| Water | 95.30 | 95.30 | 96.00 | 96.40 | 97.20 | 95.2 | 93.5 | 96.85 |
| HCl | q.s. | q.s. | q.s. | q.s. | q.s. | q.s. | q.s | |
| Total | 100.0 | 100.0 | 100.0 | 100.0 | 100.0 | 100.0 | 100.0 | 100 |

| Ingredients | Formula 16 | Formula 17 | Formula 18 | Formula 19 | Formula 20 | Formula 21 | Formula 22 | Formula 23 |
|---|---|---|---|---|---|---|---|---|
| PVP-I | 1.06 | | 3.50 | 1.00 | 3.00 | 0.50 | 0.50 | 0.50 |
| Sodium Citrate | 1.00 | 1.04 | 1.00 | 0.10 | 1.00 | 4.00 | 2.00 | 4.00 |
| Copper Sulfate penta hydrate | 1.00 | 1.00 | 0.40 | 0.05 | 0.05 | 0.01 | 0.01 | 0.01 |
| Sodium Nitrite | 0.15 | 0.10 | 1.00 | 0.10 | 0.10 | | | 0.01 |
| Potassium Iodate | | | | | | 0.01 | 0.01 | |
| Potassium Iodide (KI) | | | 0.13 | | | | | |
| Water | 96.79 | 97.86 | 93.97 | 98.75 | 95.85 | 95.48 | 97.48 | 95.48 |
| HCl | q.s | q.s | q.s | q.s | q.s | q.s | q.s | q.s |
| Total | 100 | 100 | 100 | 100 | 100 | 100 | 100 | 100 |

| Ingredients | Formula 24 | Formula 25 | Formula 26 |
|---|---|---|---|
| PVP-I | 0.50 | 2.00 | 0.50 |
| Sodium Citrate | 4.00 | 1.00 | 1.00 |
| Copper Sulfate penta hydrate | 0.00 | 0.10 | 0.10 |
| Hydrogen Peroxide | | 3.00 | 1.00 |
| Sodium Nitrite | 0.00 | 0.10 | 0.00 |
| Potassium Iodate | 0.01 | 0.00 | 0.01 |
| Potassium Iodide (KI) | | | |
| Water | 95.49 | 95.80 | 97.39 |
| HCl | q.s | q.s | q.s |
| Total | 100 | 100 | 100 |

Applications

Figure 4:
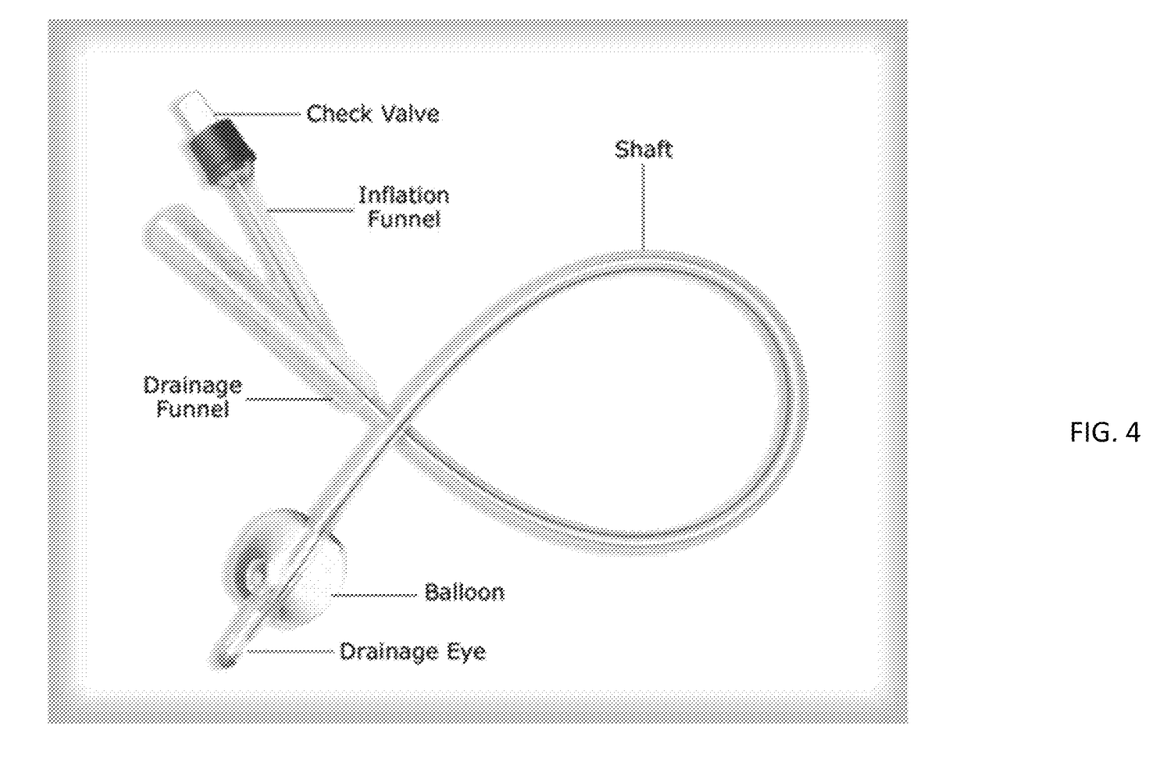
FIG. 4 shows a urinary catheter having an antimicrobial delivery system, in accordance with implementations described herein.
Figure 5:
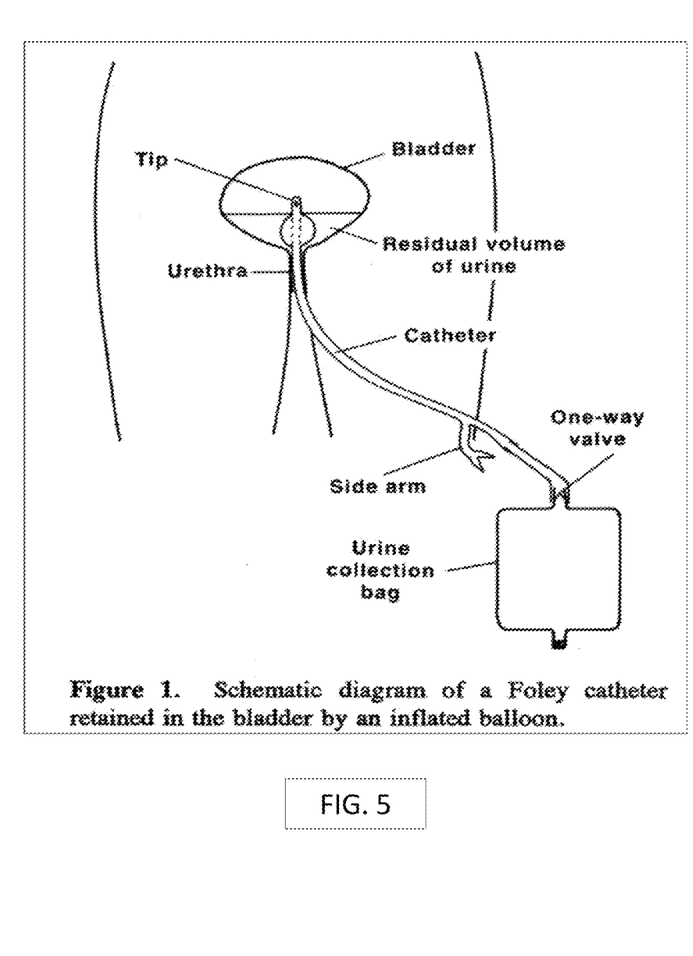
FIG. 5 illustrates the insertion and use of a urinary catheter, consistent with implementations described herein.

An antimicrobial solution as described above has many applications for infection control of HAIs. In the case of a urinary catheter (e.g., Foley catheter, as shown in FIG. 4), a system and apparatus is provided for preventing encrustation of the urine catheter in use (FIG. 5) to prevent colonization of the catheter by bacteria. In some implementations, diffusion and/or osmosis of antimicrobial agents from a solution are employed within a retention balloon of the catheter, as shown in FIG. 7. In some implementations, the urinary catheter simultaneously supplies three antimicrobial agents (free iodine, nitric oxide gas, and copper ion). In some cases, this is achieved by controlled release of antimicrobial agents in the antimicrobial solution directly into the urine from the balloon catheter and the communicating lumen itself, i.e. via diffusion and/or osmosis. This can also supply antimicrobial agents to the catheter material to impregnate the catheter material, such that the catheter material (i.e. tubing) becomes antimicrobial material to prevent the formation of a biofilm or other surface that could host bacterial growth.

Catheter materials suitable for use with the solutions described herein include polyurethane, natural rubber latex, synthetic polyisoprene latex, neoprene, styrene butadiene rubber, silicone or siliconized rubber latex material. Indwelling catheters are predominantly manufactured from natural rubber latex and silicone material. Some are made of synthetic isoprene latex or polyurethane. These polymers are suitable for manufacture of medical and surgical instruments such as endotracheal tubes, inhalation bags, intravenous catheters, centralize catheters, and urology catheters such as a Foley catheter. The two most commonly used blood-compatible materials for hemodialysis catheters are silicone and polyurethane. Medical grade silicone rubber has traditionally been considered the standard for long-term access in animals and humans. Silicone is resistant to most chemicals and is also very soft and flexible.

Figure 6:
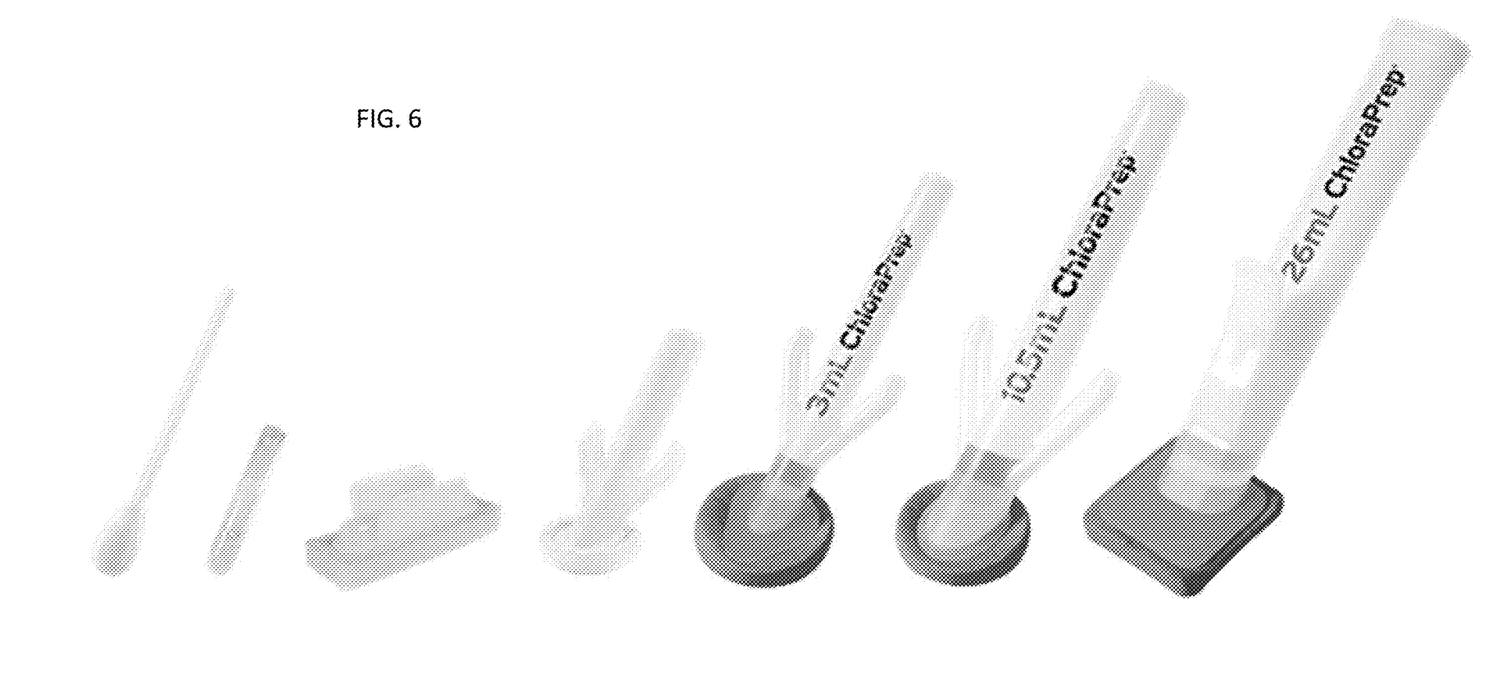
FIG. 6 illustrates various delivery devices for delivering an antimicrobial solution as described herein.

In yet other implementations, as illustrated in FIG. 6, a topical product of an antimicrobial solution, as described herein, can be applied by one of a number of applicator devices, from a swap to a foam applicator. The applicator can include a container for the antimicrobial solution.

While in some implementations, the antimicrobial components of a solution are delivered by diffusion and/or osmosis via a catheter balloon or other thin, permeable membrane or a medical device, the solution can be provided and stored in a container that inhibits such diffusion and/or osmosis. For instance, the solution can be packaged in a container with a wall thickness that inhibits any diffusion and/or osmosis, for at least a period of time, such as 2 years or more. Such a container can be made of polypropylene, polyethylene, polycarbonate or other plastic material, or any other thermoplastic polymer material of suitable thickness. Accordingly, a shelf life of the solution can be 2-3 years or more.

EXPERIMENTS AND EXAMPLES

A number of experiments were conducted using an "Iodine-Starch" test. This test is a chemical reaction that is used to test for the presence of starch or for iodine. The combination of starch and iodine is intensely blue-black in color. The interaction between starch and the triiodide anion (I-3) is the basis for iodometry.

Starch as an indicator: starch is often used in chemistry as an indicator for redox titrations where triiodide (I3−) is present. Starch forms a very dark blue-black complex solution with triiodide. However, the complex is not formed if only iodine or only iodide (I—) is present. The color of the starch complex is so deep, that it can be detected visually when the concentration of the iodine is as low as 20 µM at 20° C.

Experiment 1:

In an experiment to show that free iodine diffuses through a balloon membrane, such as may be used with a Foley catheter or other medical device, a balloon catheter was filled with an iodine solution. This iodine solution can be a tincture iodine or povidone iodine solution called iodophor. The balloon containing the iodine solution was then immersed into a water solution containing starch.

Using an iodine-starch test, a chemical reaction is allowed to slowly occur in the iodine solution. These chemical reactions release free iodine. The iodine I2 molecule diffuses through the membrane of the balloon material and reacts with the starch to make a deep blue color, the intensity of which depends on the concentration of the free iodine that diffused through the membrane.

1) At time zero, it was demonstrated that the color of the water solution outside of the balloon was clear, indicating no presence of iodine in the water solution. After each successive day of the filled balloon being submersed in the water, the color of the water turned a deeper and deeper blue color (i.e. the blue color at day 3 was darker than the blue color at day 2, which in turn was darker than the blue color at day 1). This conclusively showed the gradual escape, via diffusion and/or osmosis, of free iodine from the balloon and into the water solution over a period of time.

2) A Foley catheter has two tubes or lumens, one for filling the balloon and one for the release and conveyance of urine from a patient's bladder to a urine bag. In the experiment, both tubing was submerged in the starch/water solution. The experiment showed that the starch/water solution turned blue, showing that iodine from the balloon tubing escaped through the tubing wall and reacted with starch in the water from the other tubing.

3) In an alternative aspect of this experiment, results showed that the iodine presence in the water solution outside the balloon, at time zero, as iodine is filled in the balloon, the water color is clear indicating no escape of iodine from the balloon. After day 1 and day 2, the water solution became increasingly deeper blue; demonstrating that the free iodine molecule came from the iodine solution (PVP-I Control solution—2% PVP-I in water only) inside the balloon, diffused through the balloon membrane to react with starch in the water solution. At day 3 the water solution is darker still, showing that free iodine will continue to escape the balloon and react with starch to make the water solution an ever darker blue color.

Experiment 2:

Another experiment was conducted to show that all iodine solutions will produce free iodine that diffuses through a balloon membrane, using a urine-based solution in which a balloon is immersed.

1) This experiment showed that all the iodine solutions inside the balloon will have a chemical reaction to produce free iodine molecules of 12. The experiment showed that this free iodine will diffuse through the balloon membrane due to a difference in concentration per Le Chatelier's principle. Le Chatelier's principle states that if a stress is applied to a reaction mixture at equilibrium, the net reaction goes in the direction that relieves the stress. Change in the concentration of a reactant or product is one way to place a stress on a reaction at equilibrium. Therefore, the free iodine will slowly diffuse through the balloon membrane until all the chemical is reach to the equilibrium. In this case, when the Foley catheter balloon containing iodine solution is immersed in a urine solution, the free iodine molecule will slowly diffuse through the balloon membrane. The diffusion rate of the iodine depends on several factors, such as urine temperature, the thickness of the balloon membrane, the balloon surface area, the volume of the balloon, the volume of the iodine solution in the balloon. If we assume to keep every factor the same, the diffusion rate of iodine will depend on the formulation. For example, a tincture iodine will not be as stable as povidone iodine, so the tincture iodine will allow the chemical reaction quicker and allow the free iodine to escape faster than the PVP-I solution. Further, the Iodophor solution composed of only PVP-I in water was shown to not be stable and therefore will release the free iodine molecules faster than the Iodophor solution composed of PVP-I with a suitable pH buffer such as sodium bicarbonate, ammonium acetate, dibasic sodium phosphate, or sodium citrate.

2) As the iodine molecules diffused through the balloon membrane per Le Chatelier's principle, the urine solution slowly became darker with more and more free iodine dissolved and the iodine solution inside the balloon was slowly lighter with less iodine in it. By day 3, the iodine solution inside the balloon disappeared due to all the iodine escaping out the balloon. However, where the balloon was filled with the formula 20 or another formula containing copper there, there was still color inside the balloon.

Table 2 shows the results with respect to *Staphylococcus Aureus*.

TABLE 2

| Time Point | Start Date/Time | CFU's per ml |
|---|---|---|
| T = 0 | May 27, 2021/ 5:10 pm | $6.5 \times 10^7$ |
| T = 10 minutes | May 27, 2021/ 5:20 pm | 0 |
| T = 24 hours | May 28, 2021/ 5:20 pm | 0 |

Table 3 shows the results of other microbials.

TABLE 3

| Report Lab F21-1355-00 | | | | |
|---|---|---|---|---|
| Sample Names | T = 0 | T = 3 hrs | T = 24 hrs (1 day) | T = 72 hrs (3 days) |
| *Pseudomonas aeruginosa* (Gram Negative) | | | | |
| Positive Control | $1.1 \times 10^3$ | $3.9 \times 10^2$ | $1.6 \times 10^4$ | $2.1 \times 10^6$ |
| Negative Control | 0 | 0 | 0 | 0 |
| Neat Sample as for Bladder Irrigation | $1.3 \times 10^3$ | (No bacteria) | (No bacteria) | (No bacteria) |
| *Candida Albicans* (Yeast) | | | | |
| Positive Control | $1.7 \times 10^3$ | $1.4 \times 10^3$ | $5.0 \times 10^3$ | $2.6 \times 10^7$ |
| Negative Control | 0 | 0 | 0 | 0 |
| Neat Sample as for Bladder Irrigation | $3.6 \times 10^3$ | (No bacteria) | (No bacteria) | (No bacteria) |
| *Staphylococcus Aureus* (gram Positive) | | | | |
| Positive Control | $3.2 \times 10^3$ | $8.1 \times 10^3$ | $1.8 \times 10^8$ | $3.3 \times 10^8$ |
| Negative Control | 0 | 0 | 0 | 0 |
| Neat Sample as for Bladder Irrigation | $3.0 \times 10^3$ | (No bacteria) | (No bacteria) | (No bacteria) |
| *Enterococcus faecalis* (Gram Positive) | | | | |
| Positive Control | $3.8 \times 10^3$ | $8.5 \times 10^3$ | $1.5 \times 10^8$ | $1.1 \times 10^9$ |
| Negative Control | 0 | 0 | 0 | 0 |
| Neat Sample as for Bladder Irrigation | $3.5 \times 10^3$ | (No bacteria) | (No bacteria) | (No bacteria) |

Although a few embodiments have been described in detail above, other modifications are possible. Other embodiments may be within the scope of the following claims.

The invention claimed is:

1. An antimicrobial solution for a medical device having a balloon defined by an elastic wall that is liquid-impermeable and gas-permeable, the balloon being configured to be at least partially inserted into a patient, the antimicrobial solution comprising:
   water; and
   an amount of iodine in the water sufficient to generate free elemental iodine when the antimicrobial solution inflates the balloon to provide a vapor pressure differential to the antimicrobial solution, such that the free elemental iodine diffuses through the wall of the balloon to form an antimicrobial region proximate an outer surface of the wall of the balloon;
   wherein the solution comprises 0.01% to 1% iodine by weight and 85% to 98% water by weight.

2. The antimicrobial solution in accordance with claim 1, wherein the 0.01% to 1% iodine by weight is comprised of 0.1% to 10% povidone iodine having about 9% to 12% iodine by weight.

3. The antimicrobial solution in accordance with claim 1, further comprising:
   a water-soluble oxidizing agent; and
   water-soluble cupric salt.

4. The antimicrobial solution in accordance with claim 3, wherein the water-soluble oxidizing agent is 0.001% to 0.5% of the solution by weight, and the water-soluble cupric salt is 0.001% to 0.5% of the solution by weight.

5. The antimicrobial solution in accordance with claim 1, further comprising: a buffering agent selected from the group of buffering agents consisting of sodium acetate, ammonium acetate, sodium citrate, sodium phosphate dibasic heptahydrate, citric acid, and sodium phosphate dibasic.

6. The antimicrobial solution in accordance with claim 3, wherein the water-soluble oxidizing agent is selected from the group of oxidizing agents consisting of alkali metals nitrite, nitrate, chlorate, hydrogen peroxide and iodate.

7. The antimicrobial solution in accordance with claim 3, wherein the water-soluble cupric salt is cupric sulfate penta hydrate.

8. The antimicrobial solution in accordance with claim 1, wherein the amount of iodine by weight is provided at a volume of 2 to 20 ml.

9. An antimicrobial catheter system for a patient, the system comprising:
   a catheter device having a lumen and an inflatable balloon defined by a wall formed of an elastomeric polymer that is liquid-impermeable and gas-permeable, the inflatable balloon being configured for at least partial placement into the patient; and
   an antimicrobial solution that is introducible in a stable state into the lumen to inflate the balloon of the catheter device, the antimicrobial solution comprising 0.01% to 1% iodine by weight and 85% to 98% water by weight;
   whereupon introduction of the antimicrobial solution into the balloon provides a vapor pressure differential to the antimicrobial solution to generate free elemental iodine such that the elemental iodine diffuses through the wall of the balloon to form an antimicrobial region proximate an outer surface of the wall of the chamber.

10. The antimicrobial catheter system in accordance with claim 9, wherein the 0.01% to 1% iodine by weight is comprised of 0.1% to 10% povidone iodine having about 9% to 12% iodine by weight.

11. The antimicrobial catheter system in accordance with claim 9, wherein the antimicrobial solution further comprises:
   a water-soluble oxidizing agent; and
   water-soluble cupric salt.

12. The antimicrobial catheter system in accordance with claim 11, wherein the water-soluble oxidizing agent is 0.001% to 0.5% of the solution by weight, and the water-soluble cupric salt is 0.001% to 0.5% of the solution by weight.

13. The antimicrobial catheter system in accordance with claim 9, wherein the antimicrobial solution further comprises:
   a buffering agent selected from the group of buffering agents consisting of sodium acetate, ammonium acetate, sodium citrate, sodium phosphate dibasic heptahydrate, citric acid, and sodium phosphate dibasic.

14. The antimicrobial catheter system in accordance with claim 11, wherein the water-soluble oxidizing agent is selected from the group of oxidizing agents consisting of alkali metals nitrite, nitrate, chlorate, hydrogen peroxide and iodate.

15. The antimicrobial catheter system in accordance with claim 11, wherein the water-soluble cupric salt is cupric sulfate penta hydrate.

16. The antimicrobial catheter system in accordance with claim 9, wherein the antimicrobial solution is provided to the balloon at a volume of between 2 and 20 ml.

17. A method of disinfecting a catheter that is at least partially placed into a patient, the catheter comprising a lumen and an inflatable balloon defined by an elastic wall that is liquid-impermeable and gas-permeable, the method comprising:

introducing a locking solution into the lumen of the catheter to inflate the balloon, the locking solution comprising 0.01% to 1% iodine by weight and 85% to 98% water by weight;

generating free elemental iodine by the introduction of the locking solution into the lumen and balloon of the catheter to create a vapor pressure differential on the locking solution such that the elemental iodine diffuses through the wall of the inflated balloon to form an antimicrobial polymer on an outer surface of the wall of the inflated balloon; and     disinfecting an area on or around the lumen and the wall with the antimicrobial polymer formed on the lumen and/or the free elemental iodine diffused through the wall of the inflated balloon.

18. The method in accordance with claim 17, wherein the 0.01% to 1% iodine by weight is comprised of 0.1% to 10% povidone iodine having about 9% to 12% iodine by weight.

19. The method in accordance with claim 17, wherein the locking solution further comprises:

a water-soluble oxidizing agent; and water-soluble cupric salt.

20. The method in accordance with claim 19, wherein the water-soluble oxidizing agent is 0.001% to 0.5% of the locking solution by weight, and the water-soluble cupric salt is 0.001% to 0.5% of the locking solution by weight.

21. The method in accordance with claim 17, wherein the locking solution further comprises:

a buffering agent selected from the group of buffering agents consisting of sodium acetate, ammonium acetate, sodium citrate, sodium phosphate dibasic heptahydrate, citric acid, and sodium phosphate dibasic.

22. The method in accordance with claim 19, wherein the water-soluble oxidizing agent is selected from the group of oxidizing agents consisting of alkali metals nitrite, nitrate, chlorate, hydrogen peroxide and iodate.

23. The method in accordance with claim 19, wherein the water-soluble cupric salt is cupric sulfate penta hydrate.

24. The method in accordance with claim 17, wherein the antimicrobial solution is provided to the balloon of the Foley catheter at a volume of between 2 and 20 ml.

25. The method in accordance with claim 17, wherein the catheter is a Foley catheter configured for intra-urinary insertion.

* * * * *